United States Patent
LaCombe et al.

(10) Patent No.: US 6,814,755 B2
(45) Date of Patent: Nov. 9, 2004

(54) SYNTHETIC CORNEA

(75) Inventors: Emmanuel LaCombe, Paris (FR); Jean-Marie Parel, Miami Shores, FL (US); Bernard Duchesne, Liege (BE); Franck Villain, Annecy (FR)

(73) Assignee: Corneal Industrie, Pringy (FR)

( * ) Notice: Subject to any disclaimer, the term of this patent is extended or adjusted under 35 U.S.C. 154(b) by 160 days.

(21) Appl. No.: 10/296,773

(22) PCT Filed: Jun. 29, 1999

(86) PCT No.: PCT/US99/14986
§ 371 (c)(1), (2), (4) Date: Dec. 29, 2000

(87) PCT Pub. No.: WO01/95836
PCT Pub. Date: Dec. 20, 2001

(65) Prior Publication Data
US 2004/0088049 A1 May 6, 2004

(30) Foreign Application Priority Data
Jun. 16, 2000 (FR) .......................................... 00 07684
Jul. 20, 2000 (FR) .......................................... 00 09550

(51) Int. Cl.$^7$ .................................................. A61F 2/14
(52) U.S. Cl. ..................................... 623/5.14; 623/5.15
(58) Field of Search .............................. 623/5.11–5.16, 623/906, FOR 104; 351/174

(56) References Cited

U.S. PATENT DOCUMENTS

| | | | |
|---|---|---|---|
| 4,563,779 A | 1/1986 | Kelman | |
| 4,842,599 A | 6/1989 | Bronstein | |
| 5,152,786 A | * 10/1992 | Hanna | ........................ 623/5.11 |
| 5,300,116 A | 4/1994 | Chirila et al. | |
| 5,489,301 A | 2/1996 | Barber | |
| 5,945,498 A | 8/1999 | Hopken et al. | |

FOREIGN PATENT DOCUMENTS

| | | | |
|---|---|---|---|
| DE | 195 08 922 A1 | 3/1995 | |
| EP | 0 420 549 A2 | 9/1990 | |
| JP | 6-245944 A | * 9/1994 | ........ 623/FOR 104 |
| WO | WO 97/27824 | 8/1997 | |

OTHER PUBLICATIONS

International Preliminary Examination Report dated Jun. 18, 2002 (in French) for PCT/FR01/01845.
International Search Report dated Aug. 14, 2001 (in French) for PCT/FR01/01845.

* cited by examiner

Primary Examiner—David H. Willse
(74) Attorney, Agent, or Firm—Cohen, Pontani, Lieberman & Pavane

(57) ABSTRACT

A synthetic cornea for placing in a recess formed in the cornea, the recess opening out into the anterior face of the cornea so as to leave Descemet's membrane intact. The synthetic cornea comprises a piece (42) of flexible transparent material having an axis of circular symmetry and presenting an anterior face (44) in the form of a spherical cap of radius Ra and a posterior face (46) in the form of a spherical cap of radius Rp, the central zones of the two faces being separated by a distance e, and a side wall (48) substantially in the form of a truncated cone whose axis coincides with the axis of symmetry and whose apex lies in front of the anterior face, the angle a made between the section of the side wall and the section of the posterior face in a section plane containing the axis of revolution being less than or equal to 45°.

18 Claims, 2 Drawing Sheets

SYNTHETIC CORNEA

PRIORITY CLAIM

This is a U.S. national stage of application No. PCT/FR01/01845, filed on 14 Jun. 2001. Priority is claimed on that application and on the following application(s): Country: France, Application No.: 0007684, Filed: 16 Jun. 2000; Country: France, Application No.: 0009550, Filed: 20 Jul. 2000.

BACKGROUND OF THE INVENTION

The present invention relates to a synthetic cornea.

More precisely, the invention relates to an optical prosthesis which can be put into place in the cornea after a central opening has been formed therein when the cornea no longer performs its transparency function.

Accompanying FIG. 1 shows the central portion of the cornea 10 of an eye. It is made up of a plurality of membranes or lamellae placed one on another. Starting from the posterior face, i.e. the inside face 12 of the cornea, there can be seen the endothelium 14 which is constituted by a layer of cells that do not regenerate, Descemet's membrane 16, intermediate lamellae 18 forming the stroma of the cornea, and then Bowman's membrane 20, and finally the epithelium 22 which constitutes the anterior face 24 of the cornea. The epithelium is constituted by a plurality of layers of cells with great propensity towards regeneration. The total thickness of the cornea, in its central region, is about 500 microns ($\mu$m) and together the stroma plus the epithelium constitute 97% of the total thickness.

In known techniques for putting a keratoprosthesis into place, an incision is made in the form of a cylindrical passage 26 passing right through the thickness of the cornea. In the most widely known type of keratoprosthesis, known as intrastromal keratoprosthesis, the prosthesis is constituted by a cylindrical optical piece placed in the passage 26, and it has an annular skirt which is inserted between the lamellae 18 constituting the stroma of the cornea in order to hold the keratoprosthesis mechanically in place in the cornea. That interstromal technique of keratoprosthesis is known to give results that are poor or even clearly bad.

That is why proposals have been made in particular in patent application WO 97/27824 in the name of the Applicant, for another form of keratoprosthesis in which the cylindrical optical portion is provided with a posterior lateral skirt that is pressed against the inside face of the cornea in order to hold the keratoprosthesis mechanically in the cornea. That solution gives results that are much more satisfactory.

Whatever the way in which the keratoprosthesis is held in the cornea, prior techniques have required a passage to be made in the central portion of the cornea passing right through the cornea. The fact of making such a smooth opening presents various drawbacks, in particular concerning risks of leakage or infection.

When the cornea has been damaged in severe manner (burns, etc.), keratoprostheses with post-corneal bearing surfaces constitute the best solution.

In more numerous cases, the damage to the cornea is restricted and Descemet's membrane is not affected. A corneal graft is then possible. However, problems associated with viral contamination and with the shortage of tissue for grafting, mean that it would be advantageous to have a synthetic cornea suitable for being put into place in the cornea while still enabling Descemet's membrane to be conserved together with the endothelial layer so as to avoid the above-mentioned complications due to an opening passing through the cornea.

Document U.S. Pat. No. 4,842,599 describes a synthetic cornea which can be put into place in the cornea while conserving Descemet's membrane. However, in order to hold the synthetic cornea mechanically in place, it is provided with an annular fixing skirt, said skirt having orifices for receiving sutures. Such a solution is not satisfactory since it gives rise to a large amount of trauma over an extended zone of the cornea.

SUMMARY OF THE INVENTION

An object of the present invention is to provide a synthetic cornea suitable for putting into place in the cornea and for being held effectively therein while avoiding perforating the cornea right through, whenever the state of the posterior planes of the patient's cornea make such a solution possible.

According to the invention, this object is achieved by a synthetic cornea for placing in a recess formed in the cornea of the eye, said recess opening out into the anterior face of the cornea and not into its posterior face so as to leave Descemet's membrane intact, the synthetic cornea being characterized in that it comprises a piece of flexible transparent material having an axis of circular symmetry presenting an anterior face in the form of a spherical cap of radius Ra and a posterior face in the form of a spherical cap of radius Rp, the two faces being spaced apart in their central zones by a distance e, and a side wall substantially in the form of a truncated cone having its axis coinciding with the axis of symmetry and having its apex disposed in front of said anterior face, the angle a between the section of the side wall and the section of the posterior face in a section plane containing said axis of symmetry lying in the range 10° to 35°.

It will be understood that because the prosthesis is generally in the shape of a truncated cone, it can be received in a recess in the central portion of the cornea that is of similar shape without it being necessary to perforate Descemet's membrane and the endothelium. Nevertheless, because of its frustoconical shape, the synthetic cornea is held effectively in the cornea, pressed against Descemet's membrane. When the angle a is greater than 35°, the risk of expulsion becomes great.

The angle a is preferably about 25° to 30°, thus providing still better retention of the prosthesis in the cornea.

More preferably, the radius of curvature of the anterior face of the transparent piece is as close as possible to that of the anterior face of the cornea, i.e. it lies in the range 6.5 millimeters (mm) to 8.5 mm. This avoids any risk of disturbing movements of the eyelids over the cornea, which would be likely to interfere mechanically with retention.

Another problem which arises when placing a synthetic cornea in the natural cornea, is the risk of cell proliferation that can develop on the posterior face of the synthetic cornea, causing said posterior face to become progressively opaque by forming a retroprosthetic membrane.

In an improved embodiment of the invention, the synthetic cornea further comprises an annular skirt connected to the side face of the piece forming the synthetic cornea, the posterior face of said skirt being placed on the same spherical cap as the posterior face of the synthetic cornea proper, said skirt having a thickness of not more than 100 $\mu$m.

The skirt serves as a barrier against cell proliferation towards the posterior face of the synthetic cornea proper. It has no mechanical function of holding the synthetic cornea in the natural cornea. That is why it can be of very small thickness, less than 100 μm and preferably less than 50 μm. Since the Young's modulus used is preferably less than 1 megapascal (MPa), it will be understood that the skirt has no significant mechanical strength.

In order to further improve the barrier effect against cell proliferation, provision can be made for the edge of the skirt to be "square-cut".

Other characteristics and advantages of the invention appear more clearly on reading the following description of various embodiments of the invention given as non-limiting examples.

BRIEF DESCRIPTION OF THE DRAWINGS

The description provided in this way refers to the accompanying figures, in which.

DETAILED DESCRIPTION OF THE PRESENTLY PREFERRED EMBODIMENTS

Figure 1:
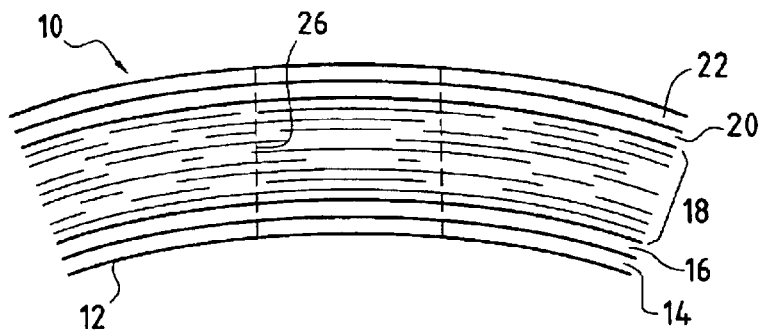
FIG. 1, described above, is a cross-section through the corneal structure of the eye.
Figure 2:
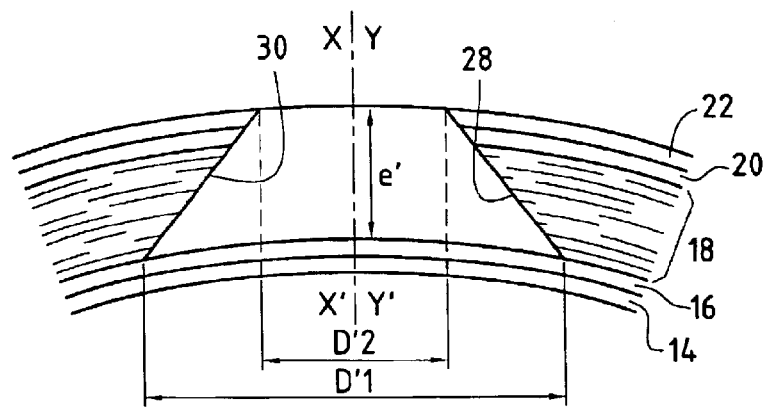
FIG. 2 shows a synthetic cornea of the invention in place in the cornea.

The synthetic cornea is for placing in a deep lamellar trepanation made in the central portion of the cornea, in front of Descemet's membrane. In FIG. 2, this recess 28 can be seen which presents an axis of circular symmetry YY'. The recess has a frustoconical wall 30 with its apex being in front of the anterior face of the cornea, and the wall stops at Descemet's membrane 16. This recess is thus of a depth e', presenting a diameter D'2 in the anterior face of the cornea, and a diameter D'1 in the vicinity of Descemet's membrane.

Figure 3:
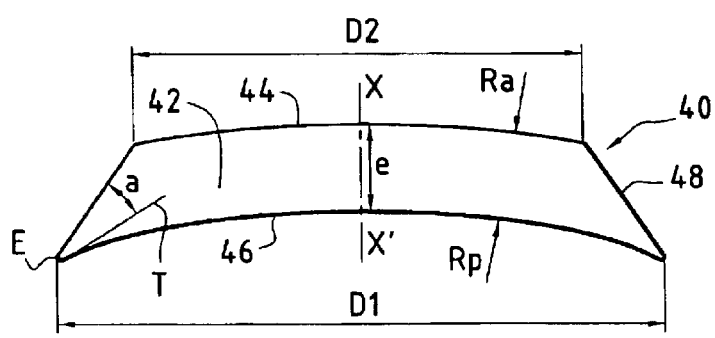
FIG. 3 is a vertical section through a preferred embodiment of the synthetic cornea.

With reference now to FIG. 3, a first embodiment of the synthetic cornea 40 is described in greater detail. In this embodiment, the synthetic cornea consists in a single piece 42 having an axis of circular symmetry XX'. The piece 42 is defined by an anterior face 44 in the form of a spherical cap of radius Ra, by a posterior face 46 likewise in the form of a spherical cap of radius Rp, and by a side wall 48 interconnecting the anterior and posterior faces 44 and 46 of the piece 42. The side wall 48 is in the form of a truncated cone whose axis is the axis XX' and whose apex lies in front of the anterior face 44 of the piece 42. The anterior face 44 is defined by a circle C2 of diameter D2 and the posterior face 46 is defined by a gcircle C1 of diameter D1. The angle a made in the proximity of the circle C1 by the connection between the side wall 48 and the posterior face 46 is shown in section on a plane containing the axis XX'.

More precisely, the angle a is the angle made in a section plane containing the axis XX' between the section of the side wall of the prosthesis and the tangent T to the section of the posterior face 46 at the point of connection E.

In order to ensure that the synthetic cornea is held properly, the angle a is less than 35°, and is preferably about 25° to 30°.

The diameter D1 preferably lies in the range 4.5 mm to 9.5 mm or 10 mm, the diameter D2 lies in the range 3 mm to 8 mm, and the distance e between the anterior and posterior faces in the central portions thereof lies in the range 400 μm to 500 μm.

The thickness e of the central portion of the prosthesis is substantially equal to the thickness of the central portion of the cornea, since all that remains thereof are Descemet's membrane and the endothelium which are of very small thickness.

The recess 28 made in the cornea is similar in shape to the piece 42, but of slightly smaller size, so that pressure is exerted on the side face of the synthetic cornea by the side edge of the housing formed in the cornea. More precisely, the diameters D'1 and D'2 are preferably 250 μm smaller than the corresponding diameters of the piece 42.

The piece 42 must be made out of a material that is biocompatible and flexible. This material may be a hydrophilic or hydrophobic acrylic. Hydrophilic acrylics can be selected from copolymers of hydroxyethyl methacrylate, of hydroxypropyl methacrylate, of hydroxybutyl methacrylate, and of hydroxyhexyl methacrylate.

For hydrophobic acrylics, it is preferable to use fluorine-containing compounds of acrylate or of methacrylate.

Hydrophobic acrylics can be obtained by copolymerizing an acrylate and a methacrylate, the acrylate having a vitreous transition temperature that is negative and the methacrylate having a transition temperature that is clearly positive (e.g. 110° C. for the methacrylate) so that the acrylic is flexible at ambient temperature.

It should be emphasized that the radii of curvature Ra and Rb of the anterior and posterior faces of the synthetic cornea are ideally selected in such a manner that these radii are substantially equal to those of the cornea, in particular so that the anterior face of the synthetic cornea lies on the same spherical cap as the anterior face of the cornea.

Nevertheless, this optimum solution cannot be satisfied, as a general rule. Firstly it is necessary for the posterior face 46 to be effectively pressed against Descemet's membrane. In order to obtain this result, it is advantageous to provide a radius of curvature that is slightly greater than that of the cornea. That is why a radius is selected that lies preferably in the range 6 mm to 8 mm.

In addition, as explained above, various materials can be used for making the synthetic cornea, and these materials have different refractive indices. For example, with some acrylics the refractive index is 1.38, i.e. very close to that of the cornea. It is then possible to give the anterior face a radius of curvature lying in the range 6.5 mm to 8.5 mm, i.e. close to that of the cornea while still retaining refractive power of 40 diopters. With other acrylics, the refractive index is 1.465. Under such circumstances, in order to conserve a refractive power of 40 diopters, it is necessary to give the anterior face a radius of curvature that is much greater, e.g. about 19 mm to 25 mm.

It will be understood that because of the frustoconical shape of the housing 28 formed in the cornea, and because of the complementary frustoconical shape of the synthetic cornea, the synthetic cornea is held mechanically in the housing whose end wall presenting the largest dimension is closed by Descemet's membrane and by the endothelium. Thus, the synthetic cornea is held effectively in the cornea even though the trepanation performed therein does not pass through. Nevertheless, in order to guarantee good integration in the period immediately following surgery, it is preferable to add adhesive, which adhesive is resorbed after a few days or a few weeks.

Figure 4:
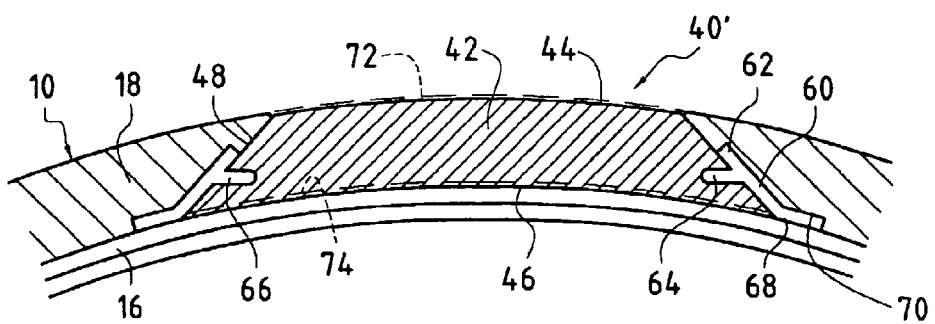
FIG. 4 shows a first variant of the synthetic cornea in place in the eye of the cornea.

With reference now to FIG. 4, there follows a description of a second embodiment of the synthetic cornea, given reference 40'. This synthetic cornea has a transparent piece 42 identical to that shown in FIG. 3 and it has a ring 60 of biocolonizable material. The ring 60 is circularly symmetrical about the axis XX' of the piece 42. It has a first frustoconical portion 62 pressed against the frustoconical side wall 48 of the piece 42. It is anchored in the piece 42 by an extension 64 which penetrates into an annular groove 66 formed in the side wall of the piece 42. This ring 60 is extended by a skirt 68 going away from the piece 42 close to its posterior face 46. The skirt 68 is for insertion in a slot 70 formed between the stroma 18 and Descemet's membrane 16.

The ring 60 is made of a biocolonizable material, and preferably out of polychlorotrifluoroethylene. The ring 60 is of a thickness of no more than 100 $\mu$m, and it is preferably 25 $\mu$m thick. The portion forming the skirt 68 of the ring 60 is preferably provided with holes having a diameter lying in the range 50 $\mu$m to 100 $\mu$m so as to improve anchoring of the ring in the cornea. The function of the ring is to encourage biocolonization after the synthetic cornea 40' has been put into place in the cornea.

It is also possible to graft a coating 72 onto the anterior face 44 of the synthetic cornea in order to facilitate cellular colonization of the prosthesis and improve its integration in the cornea. Similarly, it is possible to graft a coating 74 onto the posterior face 46 of the synthetic cornea in order to inhibit cellular proliferation, thus avoiding propagation of an epithelium associated with expulsion of the prosthesis. Naturally, the coatings 72 and 74 could be provided on the synthetic cornea 40 shown in FIG. 3.

Figure 5B:
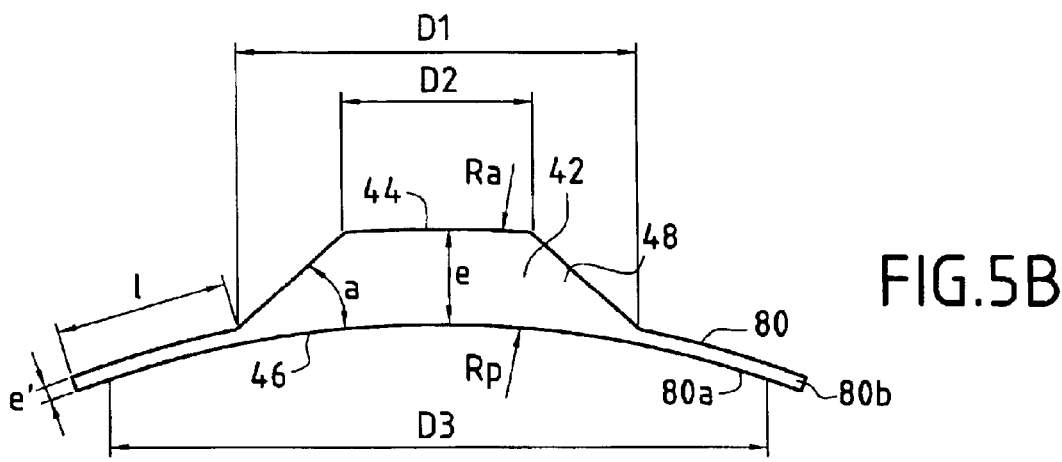
FIGS. 5A and 5B are a half-face view and a section on VB—VB showing a second variant of the synthetic cornea.
Figure 5A:
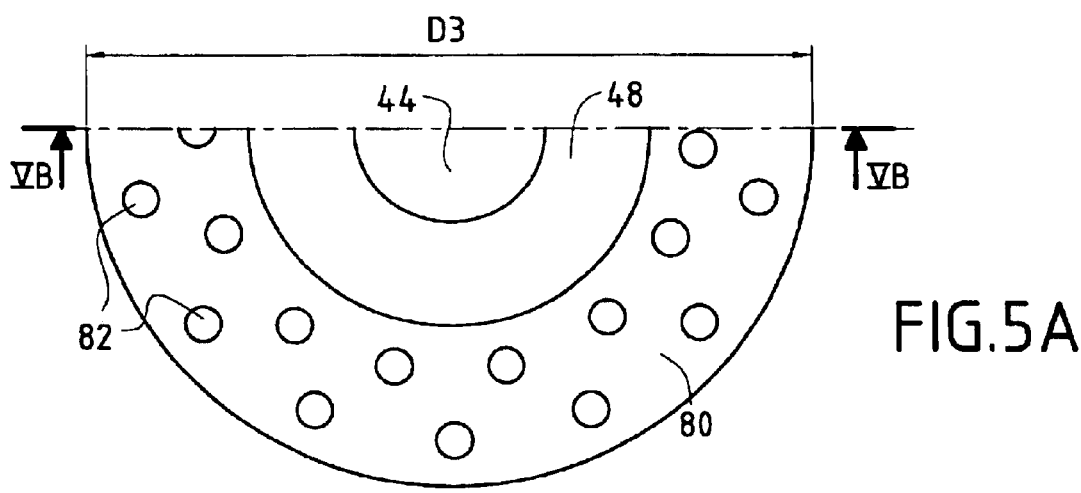

With reference now to FIGS. 5A and 5B, there follows a description of a third embodiment of the synthetic cornea. This is constituted by a piece 42 identical to those described above and by an annular skirt 80 disposed close to the posterior face 46 of the piece 42. More precisely, the posterior face of the skirt 80 is referenced 80a and lies on the same spherical cap as the posterior face 46 of the piece 42. The thickness e' of the skirt 80 lies in the range 10 $\mu$m to 100 $\mu$m, and preferably in the range 20 $\mu$m to 50 $\mu$m, while the width l of said skirt lies in the range 0.25 mm to 2.5 mm, and preferably in the range 0.75 mm to 1.5 mm. The skirt 80 is preferably provided with orifices such as 82 having a diameter lying in the range 10 $\mu$m to 100 $\mu$m, and preferably in the range 50 $\mu$m to 80 $\mu$m so as to encourage biocolonization of the holes by corneal fibrocytes and keratocytes so as to obtain long-term fixing. The holes 82 can initially be filled with an adhesive biodegradable material, e.g. fibrinogen which is capable of releasing an agent that encourages biocolonization and the formation of a bridge of collagen between the cornea's stroma and Descemet's membrane.

The skirt 80 may be made out of the same material as the optical portion or out of some other material. The material constituting the skirt 80 may be a chlorotrifluoroethylene or a tetrafluoroethylene, while the piece 42 proper is made of hydrogel.

As already explained, the synthetic cornea is held in the natural cornea because of the highly flared frustoconical shape of the piece 42. The sole function of the skirt 80 is to create a barrier against cells proliferating towards the posterior face of the synthetic cornea. It can thus be of very small thickness, typically of thickness smaller than 50 $\mu$m. This very small thickness makes it possible to reduce deformation of the cornea in the annular zone occupied by the skirt 80.

It is possible for the side edge 80b of the skirt 80 to be perpendicular to the anterior and posterior faces of the skirt. This provides "square-cut" edges which "block" cell proliferation.

The outer side surface 48 of the piece 42 and the entire surface of the skirt 80 are preferably treated to encourage and accelerate epitaxial proliferation, while the posterior face 46 of the piece 42 is treated so as to prevent such proliferation.

Figure 6:
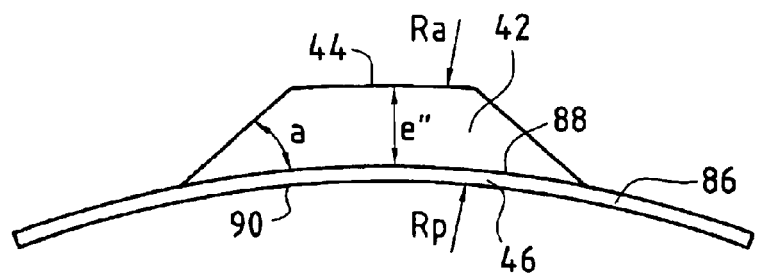
FIG. 6 is a vertical section through a third variant of the synthetic cornea.

In the embodiment shown in FIG. 6, the collar is constituted by a continuous piece 86 whose anterior central portion 88 is bonded to the posterior face 86 of the piece 42. The posterior face 90 of the piece 86 has a radius of curvature Rp corresponding to the radius of curvature of Descemet's membrane. In this case, and as explained above, the piece 42 and the assembly forming the collar 86 may be made out of the same material or out of different materials. In this case likewise, the portion of the piece 86 that is not covered by the piece 42 may advantageously have holes identical to the holes 82 shown in FIG. 5A. Finally, it is naturally the total thickness of the piece 42 plus the collar which needs to be equal to the above-mentioned value e.

This embodiment presents all of the characteristics and advantages of the embodiment of FIGS. 5A and 5B.

When the synthetic cornea is made of a hydrophobic acrylic, the acrylic is preferably selected from the group comprising heptafluorobutyl acrylate, hexafluorobutyl acrylate, and fluorine-containing compounds having a refractive index close to that of the human cornea.

What is claimed is:

1. A synthetic cornea for placing in a recess formed in the cornea of an eye, said recess opening out into the anterior face of the cornea and not into its posterior face so as to leave Descemet's membrane intact, said synthetic cornea comprising an optical portion consisting of a single piece made entirely of flexible transparent material having an axis of circular symmetry presenting an anterior face in the form of a sypherical cap of radius Ra and a posterior face in the form of a spherical cap of radius Rp, the two faces being spaced apart in central zones thereof by a distance "e", and a side wall substantially in the form of a truncated cone having its axis coinciding with the axis of symmetry and having its apex disposed in front of said anterior face in such a manner that truncated cone sections perpendicular to the axis of symmetry increase continously from a diameter D2 defining the anterior face to a diameter D1 defining the posterior face, the angle "a" between the section of the side wall and the section of the posterior face in a section plane containing said axis of symmetry lying in the range 10° to 35°.

2. A synthetic cornea according to claim 1, wherein said angle "a" is about 25° to 30°.

3. A synthetic cornea according to claim 1, wherein the distance "e" in said piece lies in the range 400 $\mu$m to 500 $\mu$m.

4. A synthetic cornea according to claim 1, wherein the diameter D2 defining the anterior face of the piece lies in the range 3 mm to 8 mm, and the diameter D1 defining the posterior face of the piece lies in the range 4.5 mm to 9.5 mm.

5. A synthetic cornea according to claim 1, wherein the radius of curvature Rp of the posterior face lies in the range 6 mm to 8 mm.

6. A synthetic cornea according to claim 1, wherein the radius of curvature Ra of said anterior face lies in the range 6.5 mm to 8.5 mm.

7. A synthetic cornea according to claim 1, wherein said material constituting said piece is a hydrophilic acrylic.

8. A synthetic cornea according to claim 7 wherein said hydrophilic acrylic is selected from the group consisting of copolymers of hydroxyethyl methacrylate, of hydroxypropyl methacrylate, of hydroxybutyl methacrylate, and of hydroxyhexyl methacrylate.

9. A synthetic cornea according to claim 1, wherein said material from which said piece is made is a hydrophobic acrylic.

10. A synthetic cornea according to claim 9, wherein said hydrophobic acrylic is selected from the group consisting of heptafluorobutyl acrylate, hexafluorobutyl acrylate, and fluorine-containing compounds having a refractive index close to that of the human cornea.

11. A synthetic cornea according to claim 1, wherein the anterior face of said piece is coated in a material that encourages cellular proliferation.

12. A synthetic cornea according to claim 1, wherein the posterior face of said piece is coated in a material that inhibits cellular proliferation.

13. A synthetic cornea according to claim 1, further comprising a circular ring made of a biocolonizable material having an inner portion secured to the side wall of said piece and having a free outer portion.

14. A synthetic cornea according to claim 13, wherein said ring is made of polychlorotrifluoroethylene.

15. A synthetic cornea according to claim 1, further comprising an annular skirt connected to the sidewall of said piece, a posterior face of said skirt being disposed on the same spherical cap as the posterior face of said piece, the thickness of said skirt being no greater than 100 $\mu$m.

16. A synthetic cornea according to claim 15, wherein said skirt is made out of the same material as said piece.

17. A synthetic cornea according to claim 15, wherein said skirt is made of a material different from that of said piece.

18. A synthetic cornea according to claim 15, wherein the thickness of said skirt lies in the range 20 $\mu$m to 50 $\mu$m.

* * * * *

UNITED STATES PATENT AND TRADEMARK OFFICE
CERTIFICATE OF CORRECTION

PATENT NO. : 6,814,755 B2  
DATED : November 9, 2004  
INVENTOR(S) : Emmanuel LaCombe Page 1 of 1

It is certified that error appears in the above-identified patent and that said Letters Patent is hereby corrected as shown below:

<u>Title page,</u>
Item [22], PCT Filed: replace with -- June 14, 2001 --.
Item [86], PCT No.: replace with -- PCT/FR01/01845
§371 (c)(1),
(2), (4) Date: Dec. 13, 2002 --.

Signed and Sealed this

Twenty-second Day of November, 2005

JON W. DUDAS
*Director of the United States Patent and Trademark Office*